US012747461B2

(12) United States Patent
Peng et al.

(10) Patent No.: US 12,747,461 B2
(45) Date of Patent: Sep. 29, 2026

(54) BACILLUS NATTO FOR PRODUCING MENAQUINONE-7 AND USE THEREOF

(71) Applicant: HUBEI MAGIC HEALTH TECHNOLOGY CO., LTD., Yichang (CN)

(72) Inventors: Xiangping Peng, Yichang (CN); Linghui Zheng, Yichang (CN); Qiong Sun, Yichang (CN); Min Zhang, Yichang (CN); Shimin Chen, Yichang (CN); Xiang Gao, Yichang (CN); Lei Shi, Yichang (CN); Chao Wang, Yichang (CN)

(73) Assignee: HUBEI MAGIC HEALTH TECHNOLOGY CO., LTD., Hubei (CN)

( * ) Notice: Subject to any disclaimer, the term of this patent is extended or adjusted under 35 U.S.C. 154(b) by 335 days.

(21) Appl. No.: 18/558,461

(22) PCT Filed: Jul. 15, 2022

(86) PCT No.: PCT/CN2022/105948
§ 371 (c)(1),
(2) Date: Nov. 1, 2023

(87) PCT Pub. No.: WO2023/284853
PCT Pub. Date: Jan. 19, 2023

(65) Prior Publication Data

US 2024/0240213 A1 Jul. 18, 2024

(30) Foreign Application Priority Data

Jul. 16, 2021 (CN) ......................... 202110805647.1

(51) Int. Cl.
*C12N 1/205* (2026.01)
*C12P 7/66* (2006.01)
*C12R 1/07* (2006.01)

(52) U.S. Cl.
CPC ................ *C12P 7/66* (2013.01); *C12N 1/205* (2021.05); *C12R 2001/07* (2021.05)

(58) Field of Classification Search
None
See application file for complete search history.

(56) References Cited

FOREIGN PATENT DOCUMENTS

| | | | |
|---|---|---|---|
| CN | 103865835 | A | 6/2014 |
| CN | 104328064 | A | 2/2015 |
| CN | 104357355 | A | 2/2015 |
| CN | 108410775 | A | 8/2018 |
| CN | 113564071 | A | 10/2021 |
| WO | 2021000246 | A1 | 1/2021 |

OTHER PUBLICATIONS

International Search Report for PCT/CN2022/105948, mailed Oct. 18, 2022, 8 pages.
Written Opinion of the ISA for PCT/CN2022/105948, mailed Oct. 18, 2022, 4 pages.

*Primary Examiner* — Richard G Hutson
(74) *Attorney, Agent, or Firm* — NIXON & VANDERHYE, PC

(57) ABSTRACT

The present invention provides *Bacillus* natto for producing menaquinone-7. *Bacillus* natto is deposited at the China General Microbiological Culture Collection Center, the accession number being CGMCC No. 21799. The strain has few requirements for nutrients, has a high yield, has mild metabolism, is easy to regulate and control, and is suitable for industrial scale-up.

15 Claims, 2 Drawing Sheets

Specification includes a Sequence Listing.

BACILLUS NATTO FOR PRODUCING MENAQUINONE-7 AND USE THEREOF

This application is the U.S. national phase of International Application No. PCT/CN2022/105948 filed Jul. 15, 2022, which designated the U.S. and claims priority to CN Patent Application No. 202110805647.1 filed Jul. 16, 2021, the entire contents of each of which are hereby incorporated by reference.

REFERENCE TO SEQUENCE LISTING SUBMITTED ELECTRONICALLY

The content of the electronically submitted sequence listing (Name: 8575-46_Amended Sequence Listing-P08020220634US.xml, Size: 3,181 bytes, and Date of Creation: Oct. 13, 2023) is herein incorporated by reference in its entirety.

TECHNICAL FIELD

The present invention relates to the technical field of microorganisms, and in particular to a *Bacillus* natto strain for producing menaquinone-7 and use thereof.

BACKGROUND

Vitamin K2 (2-methyl-3-all-trans-polyprenyl-1,4-naphthoquinones) or menaquinone series is a family of isopentenyl derivatives. The number of isoprene residues each consisting of 5 carbon atoms can be used to distinguish compounds of the menaquinone series. The nomenclature is based on the number of prenyl groups, for example, "menaquinone" or "MK" followed by the number of the groups. Although menaquinones have been found to have up to 15 prenyl groups on their side chains, only menaquinones containing 2 to 13 prenyl groups are present in human and animal tissues. Demethylated menaquinone, i.e., menaquinone unbound at carbon atom No. 2, has also been found.

Vitamin K2 is known by its generic or common name, menaquinone, and its essential components are menaquinone-4 (MK-4) and menaquinone-7 (MK-7). MK-7 is known to be one of the most active vitamin K2 series.

In the prior art, methods for producing MK-7 include: (1) chemical synthesis, which requires the use of organic solvents, thus not only being insufficiently friendly to the environment and operators but also having organic solvent residues in the resultant product and the co-existence of MK-7 with cis-trans structure in the product: (2) extraction from solid fermented natto, which has no market competitiveness due to the extremely low content of MK-7 in natto: and (3) liquid fermentation using natural *Bacillus* natto, which has a long period and low yield.

During the fermentation production of MK-7 using *Bacillus* natto, the original strain is very vigorous in growth and metabolism, and a large number of spores are very easily formed, leading to the cessation of product synthesis. In order to solve this problem, large consumption of nutrients must be provided, which makes the regulation of growth and metabolism very difficult. In addition, these heavily consumed nutrients are converted into by-products in large amounts, resulting in a viscous fermentation broth, which on the one hand is not conducive to the entry of oxygen into the fermentation broth, making it difficult to control the dissolved oxygen, and on the other hand, leads to difficulties in subsequent isolation and purification. Furthermore, differences in fermentation equipment and culture conditions (such as dissolved oxygen) result in very poor process repeatability. These reasons mentioned above make large-scale production difficult to achieve.

SUMMARY

In order to obtain *Bacillus* natto with high yield, less nutrient requirement, mild metabolism, easy regulation, and suitability for industrial scale-up, the present invention provides a *Bacillus* natto strain HDCC00023, preserved in the China General Microbiological Culture Collection Center on Feb. 1, 2021, with an accession number of CGMCC NO. 21799.

Provided is use of the *Bacillus* natto strain in preparing menaquinone-7:

or preparing one or more of a medicament, a healthcare product, a food, a beverage, a cosmetic product, an additive, and a feed comprising menaquinone-7.

Provided is a fermentation broth comprising the *Bacillus* natto strain.

Provided is use of the fermentation broth in preparing menaquinone-7:

or preparing one or more of a medicament, a healthcare product, a food, a beverage, a cosmetic product, an additive, and a feed comprising menaquinone-7.

Provided is a fermentation method for producing menaquinone-7 by using the *Bacillus* natto strain. Preferably, the fermentation method comprises performing a fermentation in a fermentation medium comprising an assimilable carbon source and/or nitrogen source.

Preferably, the assimilable carbon source is selected from one of or a combination of any of starch, maltodextrin, glucose, sucrose, lactose, maltose, industrial molasses, glycerol, soybean oil, sorbitol, and mannitol: preferably glycerol and starch.

Preferably, the assimilable nitrogen source is selected from one of or a combination of any of yeast extract powder, yeast powder, yeast cream, soybean lecithin, soybean cake powder, cottonseed cake powder, peanut cake powder, gluten powder, corn steep liquor dry powder, soybean meal, peptone, urea, and ammonium salt: preferably soy bean peptone.

Preferably, the fermentation medium further comprises an inorganic salt, wherein the inorganic salt is selected from one of or a combination of any of trisodium citrate, potassium dihydrogen phosphate, dipotassium hydrogen phosphate, ammonium sulfate, calcium carbonate, ferrous sulfate, zinc sulfate, copper sulfate, sodium chloride, potassium chloride, calcium chloride, magnesium sulfate, ferric chloride, and manganese sulfate: preferably potassium dihydrogen phosphate, magnesium sulfate, potassium chloride, and calcium chloride.

Preferably, the seed solution is fermented in the fermentation medium, with an amount of dissolved oxygen of a fermentation broth controlled to be not less than 5% or to be 5%-15%.

Preferably, the seed solution is fermented in the fermentation medium, with a total residual sugar concentration of a fermentation broth maintained to be not less than 1.0% or to be 1.0%-1.5%. Preferably, the seed solution is fermented in the fermentation medium, and the fermentation is performed at a temperature of not lower than 10° C. or not lower than 20° C., or a temperature of 20-60° C., or 20-50° C., or 20-40° C., or 30-50° C., or 30-40° C., or 35-40° C., or 37° C.

Preferably, the fermentation is performed for a period of not less than 12 h, or not less than 1 day, or not less than 2 days, or not less than 3 days, or not less than 4 days, or not less than 5 days, or not less than 6 days, more preferably performed for a period of 7 days.

Preferably, the seed solution is the primary seed solution or the secondary seed solution.

Preferably, the primary seed is prepared by taking activated single colonies, scraping the colonies, inoculating the colonies into a triangular flask, and culturing with shaking on a shaker, with the OD value controlled to be ≥4.0; the secondary seed is prepared by taking the primary seed and inoculating the primary seed into a seed tank, with the amount of dissolved oxygen controlled to be ≥40% and the OD value controlled to be ≥6.0.

Preferably, the primary seed is prepared by taking activated single colonies, scraping the colonies, inoculating the colonies into a triangular flask, and culturing with shaking on a shaker, with the OD value controlled to be ≥4.0, wherein the culture is performed at a temperature of not lower than 10° C. or not lower than 20° C., or a temperature of 20-60° C., or 20-50° C., or 20-40° C., or 30-50° C., or 30-40° C., or 35-40° C., or 37° ° C., and the culture is performed for a period of not less than 0.5 h, or not less than 1 h, or not less than 2 h, or not less than 3 h, or not less than 4 h, or not less than 5 h, or not less than 6 h, or not less than 7 h, or performed for a period of 8 h;

preferably, the secondary seed is prepared by taking the primary seed and inoculating the primary seed into a seed tank, with the amount of dissolved oxygen controlled to be ≥40% and the OD value controlled to be ≥6.0, wherein the culture is performed at a temperature of not lower than 10° C. or not lower than 20° C., or a temperature of 20-60° C., or 20-50° C., or 20-40° C., or 30-50° C., or 25-45° C., or 30-45° C., or 30-40° C., or 35-45° C., or 35-40° C., or 37° C., and the culture is performed for a period of not less than 0.5 h, or not less than 1 h, or not less than 2 h, or not less than 3 h, or not less than 4 h, or not less than 5 h, or not less than 6 h, or performed for a period of 7 h or 8 h.

Preferably, the secondary seed is prepared by taking the primary seed and inoculating the primary seed into a seed tank with a tank pressure of 0.05 MPa, with the amount of dissolved oxygen controlled to be ≥40% and the OD value controlled to be ≥6.0.

Preferably, the secondary seed is prepared by taking the primary seed and inoculating the primary seed into a seed tank with a tank pressure of 0.05 MPa and an air flow rate of 1 vvm, with the amount of dissolved oxygen controlled to be ≥40% and the OD value controlled to be ≥6.0.

Preferably, the secondary seed is prepared by taking the primary seed and inoculating the primary seed into a seed tank at a ratio of 0.02%-0.2% (V/W), more preferably at a ratio of 0.05% (V/W). Preferably, the fermentation medium comprises, by mass percent, 2% of glycerol, 5% of soluble starch, and 2% of soybean peptone.

Preferably, the fermentation method further comprises adding a feeding medium.

Preferably, the feeding medium comprises, by mass percent, 30% of maltodextrin and 10% of soybean peptone.

Preferably, when the total sugar drops below 1.5%, feeding is started.

Preferably, the seed solution is inoculated into a fermenter containing a liquid fermentation medium at a ratio of 4% (V/W), the temperature is set at 37° C., the tank pressure is set at 0.05 MPa, the air flow rate is set at 0.7 vvm, and when the amount of dissolved oxygen drops below 15%, stirring is controlled so that the amount of dissolved oxygen is 5%-15%. When the total sugar drops below 1.5%, feeding is started to control the total sugar concentration to be 1.0%-1.5%.

Beneficial Effects

1. The strain of the present invention is obtained by mutagenesis, which produces more MK-7 with a significantly improved effective conversion rate under the condition of consuming very few nutrients.

2. Due to the reduced viscosity of the feeding liquid, the dissolved oxygen in the entire fermentation process is controllable, and because it is not necessary to carry out at a high rotation speed frequently, the machine loss and energy consumption are correspondingly reduced.

3. Furthermore, the reduced viscosity of the fermentation broth makes the difficulty of subsequent purification correspondingly reduced.

4. The strain (HDCC00023) has a more moderate consumption of nutrients, and its fermentation process is easier to control.

5. The strain (HDCC00023) has stronger activity and can realize continuous fermentation production.

DETAILED DESCRIPTION

Figure 1:
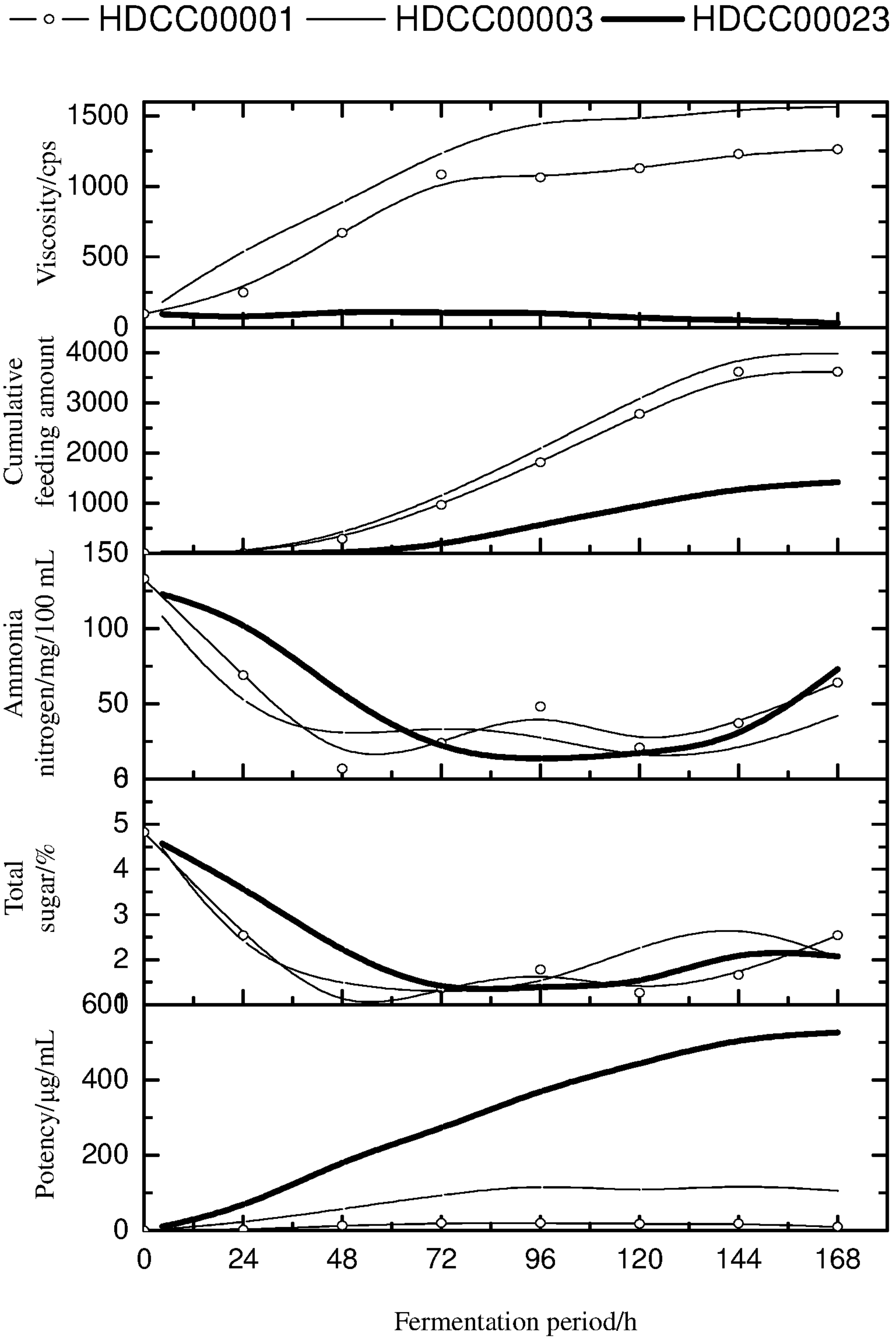
FIG. 1 shows a comparison of fermentation yield, substrate consumption, and by-product formation (viscosity characterization) of different strains in 50 L fermenters.

Unless otherwise specified, the experimental methods used in the following examples are all conventional methods.

Unless otherwise specified, the materials, reagents, and the like used in the following examples are all ordinary and commercially available products that can be purchased in the market.

The present invention will be further described by way of the examples below, and these descriptions are not intended to further limit the content of the present invention. It should be appreciated by those skilled in the art that equivalent substitutions or corresponding modifications made to the content of the present invention still fall within the scope of the present invention. Unless otherwise specified, in the culture media used in the following examples, the units of measurement for the percentages (%) used for the proportion of materials are all mass percentages.

Example 1: Mutagenesis Screening of Strains

A pure strain (HDCC00001) producing MK-7 was isolated from the feces of an adult who ate natto throughout the year. The strain was identified as *Bacillus* natto by 16SRNA sequencing (the sequence is set forth in SEQ ID NO: 1 in detail). Using adult feces as a source of isolation, the strain obtained has higher safety and is more suitable for the production of healthcare products. 0.1 mL of a thawed liquid of the original strain (HDCC00001) in a glycerol tube obtained after isolation was taken, inoculated into 50 mL of an LB liquid medium, and then cultured overnight at 37° C. The seed solution was mutagenized for 30 s using lithium chloride with a final concentration of 0.2%, serially diluted to 10-2-10-5 with sterile normal saline, then separated in an LB solid plate medium, and cultured for 24 h at a constant temperature of 37° ° C. in the dark. After colonies grew out, the colonies were transferred to a fresh LB solid medium using a toothpick and then cultured overnight at 37° ° C. The seed was then inoculated into a test tube (15 mL) containing 3 mL of a liquid primary screening fermentation medium using an inoculating needle, and then the tube was shaken for 96 h at 37° C. and 250 rpm, followed by addition of an equal volume of analytical pure isopropanol for soaking. After the mixture was centrifuged, the supernatant was taken for potency determination, and finally, an MK19283 strain was obtained, which had a fermentation level of 112 μg/mL for the primary screening in the test tube.

The MK19283 strain in a glycerol tube was taken, serially diluted to 10-3-10-6 with sterile normal saline, then separated in an LB solid plate medium, and cultured for 24 h at a constant temperature of 37° ° C. After colonies grew out, 40 colonies were randomly selected, then each inoculated in one loop into a seed flask containing 20 mL of a liquid LB medium using an inoculating needle, and then cultured overnight at 37° C. and 250 rpm. The seed was then inoculated into a 250 ml triangular flask containing 30 mL of a liquid re-screening fermentation medium at a ratio of 4% (v/v), and then the flask was shaken for 96 h at 37° C. and 250 rpm. 1 mL of the fermentation broth was taken, followed by addition of an equal volume of analytical pure isopropanol for soaking. After the mixture was centrifuged, the supernatant was taken for potency determination. Highly productive strains were selected, and natural isolation and purification were continuously performed using the method described above until the fermentation level of each colony was stable. After three consecutive rounds of purification, a strain (HDCC00003) was obtained, which had a maximum shake-flask fermentation level of 228 μg/mL, and the distribution range of shake-flask fermentation levels for 40 single colonies was 200±10 μg/mL.

0.1 mL of a thawed liquid of the HDCC00003 strain in a glycerol tube was taken, inoculated into 50 mL of an LB liquid medium, and cultured overnight at 37° C. After the seed solution was centrifuged, the bacteria were collected and resuspended in normal saline. The bacterial suspension was mutagenized for 10 s under a 15 W ultraviolet lamp and then mutagenized for another 10s using lithium chloride with a final concentration of 0.2%. By referring to the isolation and purification method for the obtained strain (HDCC00003) described above, a strain (HDCC00023) was obtained, which had a maximum shake-flask fermentation level of 584 μg/mL, and the distribution range of shake-flask fermentation levels for 40 single colonies was 564±20 μg/mL. The strain has been preserved in the China General Microbiological Culture Collection Center on Feb. 1, 2021, with an accession number of CGMCC NO. 21799.

Primary screening fermentation medium: 1% of glycerol, 0.5% of soybean peptone, pH 7.0, sterilized at 121° C. for 15 min, 3 mL/15 mL.

Re-screening fermentation medium: 4% of glycerol, 1.5% of soybean peptone, pH 7.0, sterilized at 121° ° C. for 20 min, 30 mL/250 mL.

Example 2: Fermentation Test of Primary Strain (HDCC00001) in 50 L Fermenter

1. Strain Activation

The original strain (HDCC00001) in a glycerol tube was taken and thawed at room temperature. 0.1 mL of the bacterial suspension was pipetted, inoculated onto an LB solid plate, plated uniformly, and then cultured in an incubator at 37° ° C. for 16 h to obtain activated single colonies.

2. Preparation of the Primary Seed

The activated single colonies were taken, and a loop of the colonies was scraped and then inoculated into a 500 mL triangular flask containing 100 mL of an LB liquid medium using an inoculating loop. The triangular flask was then wrapped well and placed on a shaker at 37° C. and 250 rpm for 8 h of shaking culture, with the OD value of the seed solution controlled to be ≥4.0. The pH of the LB liquid medium was adjusted to 7.0 before sterilization, wherein the conditions for the sterilization were 121-123° C. and 30 min.

3. Preparation of the Secondary Seed

Qualified primary seed was taken and inoculated into a seed tank containing 10 L of an LB liquid medium at a ratio of 0.05% (V/W), the temperature was set at 37° C., the tank pressure was set at 0.05 MPa, and the air flow rate was set at 1 vvm. Initial stirring was performed at 100 rpm, and the amount of dissolved oxygen was controlled to be ≥40% with a stirring linkage. The culture period was 7 h, with the OD value of the seed solution controlled to be ≥6.0.

The pH of the LB liquid medium was adjusted to 7.0 before sterilization, wherein the conditions for the sterilization were 121-123° C. and pressure-holding for 30 min.

4. Fermentation Culture

Qualified secondary seed was taken and inoculated into a fermenter containing 30 L of a liquid fermentation medium at a ratio of 4% (V/W), the temperature was set at 37° C., the tank pressure was set at 0.05 MPa, and the air flow rate was set at 0.7 vvm. Initial stirring was performed at 150 rpm, and when the dissolved oxygen dropped below 15%, the stirring linkage was turned on to control the amount of dissolved oxygen to be 5%-15%. The total residual sugar concentration was maintained to be 1.0%-1.5%, and the fermentation period was 7 days.

The formulation of the liquid fermentation medium was as follows: 2% of glycerol, 5% of soluble starch, and 2% of soybean peptone, with the pH adjusted to 8.0 before sterilization, wherein the conditions for the sterilization were 121-123° C. and pressure-holding for 30 min.

5. Index Monitoring During Fermentation

Since the beginning of fermentation, samples were taken every 12 h to determine the total sugar, amino nitrogen, and potency, and the statistical recording of the feeding amount was completed. According to the fermentation process and results of the strain and referring to FIG. 1 and FIG. 2, the strain (HDCC00001) had a maximum potency of 20.3 μg/mL after 3 days of fermentation, and then the amount of dissolved oxygen rebounded rapidly, the CER (which refers to the amount of carbon dioxide released from the cultures in the biological fermentation process) dropped completely to zero, a large number of spores were formed as determined by microscopic examination, and the potency no longer increased. After a large amount of feeding, the CER appeared to rebound and the amount of dissolved oxygen dropped, indicating that the activity of the bacteria was recovered, but the potency still could not be effectively increased, and even fell backward. Meanwhile, by-products were continuously accumulated, so that the viscosity of the feeding liquid was continuously increased along with the extension of the fermentation culture period, resulting in a poorer mass transfer effect of the fermentation broth.

Example 3: Fermentation Test of Mutagenized Strain (HDCC00003) in 50 L Fermenter The procedures in this example were the same as those in Example 2 except that the strain was a mutagenized strain (HDCC00003).

Figure 2:
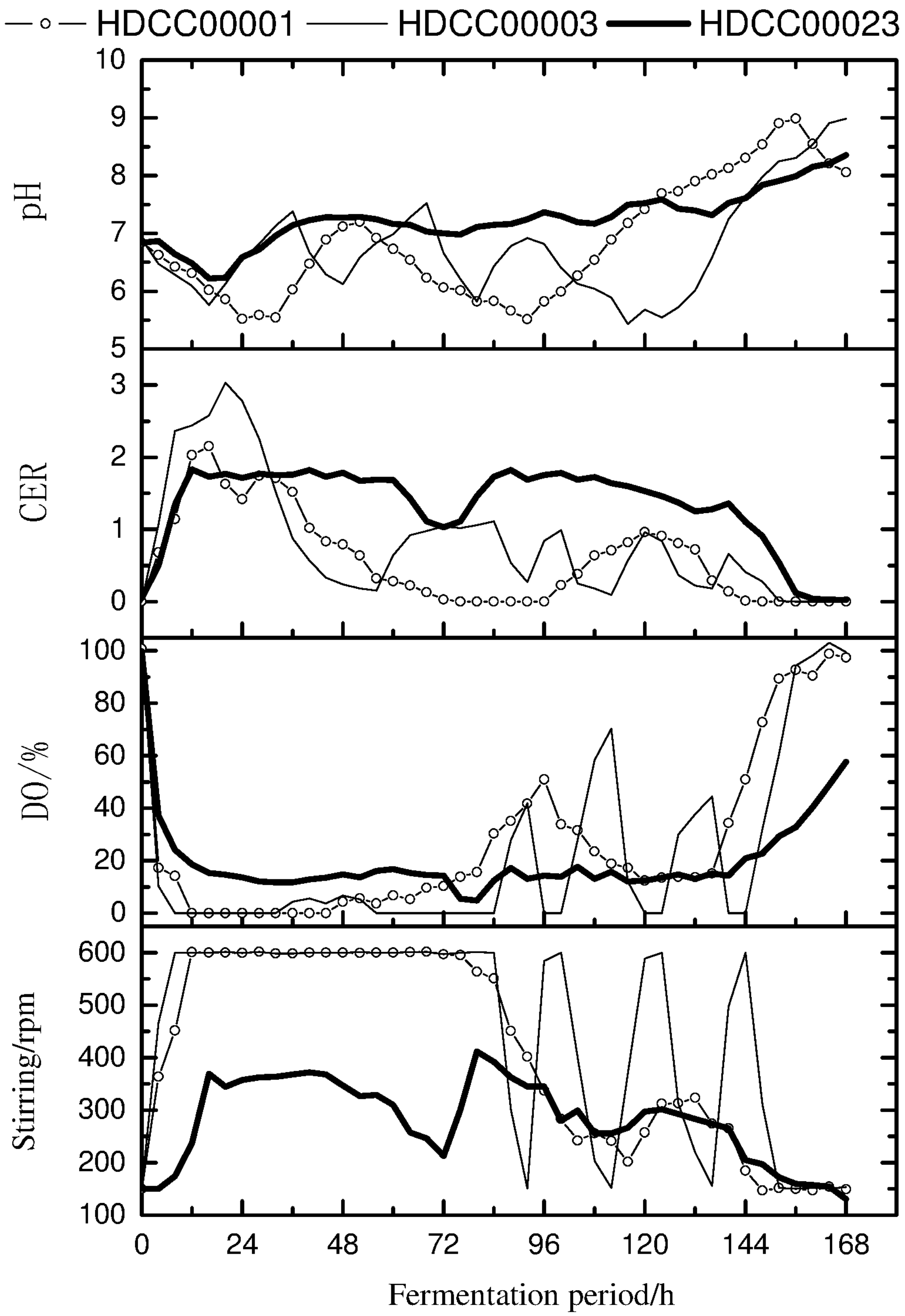
FIG. 2 shows a comparison of the parameters of the fermentation process of different strains in 50 L fermenters.

According to the fermentation process and results of the strain and referring to FIG. 1 and FIG. 2, the fermentation period of the strain (HDCC00003) could be extended to 4 days, after which the maximum potency of 124 μg/mL was achieved. In the mid-prophase of fermentation, the carbon and nitrogen sources were rapidly consumed, the amount of dissolved oxygen dropped rapidly to zero, the stirring was carried out at the maximum rotation speed, and the feeding amount was increased sharply. The results of microscopic examination showed that the increase in the feeding amount was effective in avoiding the formation of spores, but was still unable to maintain the rate of increase in potency. In addition, the curves of stirring, dissolved oxygen, and CER in the fermentation process showed that the fermentation parameters fluctuated repeatedly after 84 h, indicating that although the potency of the strain obtained after mutagenesis with lithium chloride was improved, the fermentation process of the strain was poor in stability, resulting in the difficulty in scale-up control.

Example 4: Fermentation Test of Mutagenized Strain (HDCC00023) in 50 L Fermenter The procedures in this example were the same as those in Example 2 except that the strain was a mutagenized strain (HDCC00023).

According to the fermentation process and results of the strain and referring to FIG. 1 and FIG. 2, the effective fermentation period of the strain (HDCC00023) could last for 7 days, and the fermentation potency could be continuously increased, reaching a maximum of 526 μg/mL, thus successfully demonstrating the production capacity of the strain exhibited in the shake-flask fermentation. A comparison between the potency and cumulative feeding revealed that the strain (HDCC00023) consumed the least nutrients and produced the most MK-7 compared with the strain (HDCC00003) and the strain (HDCC00001). However, the viscosity of the feeding liquid was maintained at the level of about 100 cps, indicating that the formation of by-products was effectively controlled. That is, the strain (HDCC00023) produced more MK-7 with a significantly improved effective conversion rate under the condition of consuming very few nutrients.

The difficulty of the entry of oxygen into the fermentation broth was reduced due to the reduction of the viscosity of the feeding liquid, making it easier to control the dissolved oxygen through stirring, thus eliminating the need to frequently increase the stirring speed to maintain dissolved oxygen. The required amount of dissolved oxygen could be achieved by maintaining the stirring speed at about 400 rpm, and the dissolved oxygen in the entire fermentation process was controllable. In addition, because it was not necessary to carry out at a high rotation speed frequently, the machine loss and the energy consumption were correspondingly reduced. Furthermore, the reduced viscosity of the fermentation broth made the difficulty of subsequent purification correspondingly reduced.

The CER was relatively stable and a large number of spores are not formed throughout the microscopic examination, indicating that the strain (HDCC00023) had stronger activity and could realize continuous fermentation production. In addition, the fluctuation amplitude of pH can reflect the stability of the strains in metabolizing nutrients. The strain (HDCC00023) had a more moderate consumption of nutrients as reflected by the small fluctuation amplitude of pH, so the fermentation process of the strain (HDCC00023) was easier to control compared with other strains.

Example 5: Fermentation Test of Mutagenized Strain (HDCC00023) in 30-Ton (T) Fermenter 1. Strain Activation The production strain (HDCC00023) in a working glycerol tube was taken and thawed at room temperature. 0.1 mL of the bacterial suspension was pipetted, inoculated onto an LB solid plate, plated uniformly, and then cultured in an incubator at 37° C. for 16 h to obtain activated single colonies.

2. Preparation of the Primary Seed

The activated single colonies were taken, and a loop of the colonies was scraped and then inoculated into a 2800 mL triangular flask containing 500 mL of an LB liquid medium using an inoculating loop. The triangular flask was then wrapped well and placed on a shaker at 37° C. and 220 rpm for 8 h of shaking culture, with the OD value of the seed solution controlled to be ≥4.0. The pH of the LB liquid medium was adjusted to 7.0 before sterilization, wherein the conditions for the sterilization were 121-123° C. and 30 min.

3. Preparation of the Secondary Seed

Qualified primary seed was taken and inoculated into a seed tank containing 2 tons of an LB liquid medium at a ratio of 0.05% (V/W), the temperature was set at 37° C., the tank pressure was set at 0.05 MPa, and the air flow rate was set at 1 vvm. Initial stirring was performed at 100 rpm, and the amount of dissolved oxygen was controlled to be ≥40% with a stirring linkage. The culture period was 7 h, with the OD value of the seed solution controlled to be ≥6.0.

The pH of the LB liquid medium was adjusted to 7.0 before sterilization, wherein the conditions for the sterilization were 121-123° C. and pressure-holding for 30 min.

4. Fermentation Culture

Qualified secondary seed was taken and inoculated into a fermenter containing 20 tons of a liquid fermentation medium at a ratio of 4% (V/W), the temperature was set at 37° C., the tank pressure was set at 0.05 MPa, and the air flow rate was set at 0.7 vvm. Initial stirring was performed at 80 rpm, and when the amount of dissolved oxygen dropped below 15%, the stirring linkage was turned on to control the dissolved oxygen to be 5%-15%. The total sugar concentration was controlled to be 1.0%-1.5%, and the fermentation period was 7 days.

The formulation of the liquid fermentation medium was as follows: 2% of glycerol, 5% of soluble starch, and 2% of soybean peptone, with the pH adjusted to 8.0 before sterilization, wherein the conditions for the sterilization were 121-123° C. and pressure-holding for 30 min.

The results of the fermentation culture showed that, after the strain (HDCC00023) was scaled up to 30 T scale, the process was stable and controllable with good reproducibility, and the effective fermentation period could last for more than 7 days with a fermentation potency up to 384 μg/mL.

In conclusion, the strain (HDCC00023) had a much higher potency than that of the strain (HDCC00003) and the strain (HDCC00001), and its fermentation potency could be continuously increased; the formation of by-products was effectively controlled, the growth and metabolism were mild, the dissolved oxygen in the entire fermentation process was controllable, the control of nutrient feeding was easier, and the process stability was good, so that the strain (HDCC00023) is suitable for industrial scale-up. The present invention fundamentally solves the key challenges of difficulty in scale-up (poor repeatability of process regulation), low effective conversion rate of substrate, and high production cost in the industrialization process of MK-7, and reduces the difficulty of purification of fermentation broth.

There are a variety of fermentation methods for producing MK-7 using *Bacillus* natto in the prior art, and the above examples are used only for exemplary illustration of the fermentation method employed for the *Bacillus* natto strain provided by the present invention. It can be understood that, after learning the *Bacillus* natto strain provided by the present invention, those skilled in the art can utilize the *Bacillus* natto strain provided herein for the fermentation production of MK-7 and other products (e.g., the seed solution, fermentation broths, fermentation products, and bacterial residues), and utilize the *Bacillus* natto strain provided herein or the MK-7 or other products produced therefrom for the production of other products, such as the manufacture of medicaments, healthcare products, foods, beverages, cosmetic products, additives, and feeds.

The invention claimed is:

1. A *Bacillus* natto strain HDCC00023, which is preserved in the China General Microbiological Culture Collection Center on Feb. 1, 2021, with an accession number of CGMCC NO. 21799.

2. A method of preparing menaquinone-7;
or preparing one or more of a medicament, a healthcare product, a food, a beverage, a cosmetic product, an additive, and a feed comprising menaquinone-7;
the method comprising culturing the *Bacillus* natto strain according to claim 1 to obtain menaquinone-7.

3. A fermentation broth comprising the *Bacillus* natto strain according to claim 1.

4. A method of preparing menaquinone-7;
or preparing one or more of a medicament, a healthcare product, a food, a beverage, a cosmetic product, an additive, and a feed comprising menaquinone-7;
the method comprising culturing the *Bacillus* natto strain of claim 1 in fermentation broth to obtain menaquinone-7.

5. A fermentation method for producing menaquinone-7, comprising fermenting a seed solution comprising the *Bacillus* natto strain according to claim 1 in a fermentation medium.

6. The fermentation method according to claim 5, wherein the fermentation medium comprises an assimilable carbon source and/or nitrogen source.

7. The fermentation method according to claim 6, wherein the assimilable carbon source is selected from one of or a combination of any of starch, maltodextrin, glucose, sucrose, lactose, maltose, industrial molasses, glycerol, soybean oil, sorbitol, and mannitol.

8. The fermentation method according to claim 7, wherein the assimilable carbon source is selected from one of or a combination of glycerol and starch.

9. The fermentation method according to claim 6, wherein the assimilable nitrogen source is selected from one of or a combination of any of yeast extract powder, yeast powder, yeast cream, soybean lecithin, soybean cake powder, cottonseed cake powder, peanut cake powder, gluten powder, corn steep liquor dry powder, soybean meal, peptone, urea, and ammonium salt.

10. The fermentation method according to claim 9, wherein the assimilable nitrogen source is peptone.

11. The fermentation method according to claim 6, wherein the fermentation medium further comprises an inorganic salt, wherein the inorganic salt is selected from one of or a combination of any of trisodium citrate, potassium dihydrogen phosphate, dipotassium hydrogen phosphate, ammonium sulfate, calcium carbonate, ferrous sulfate, zinc sulfate, copper sulfate, sodium chloride, potassium chloride, calcium chloride, magnesium sulfate, ferric chloride, and manganese sulfate.

12. The fermentation method according to claim 11, wherein the inorganic salt is selected from one of or a combination of any of potassium dihydrogen phosphate, magnesium sulfate, potassium chloride, and calcium chloride.

13. The fermentation method according to claim 5, wherein the seed solution is fermented in the fermentation medium, with an amount of dissolved oxygen of a fermentation broth controlled to be not less than 5% or to be 5%-15%.

14. The fermentation method according to claim 5, wherein the seed solution is fermented in the fermentation medium, with a total residual sugar concentration of a fermentation broth maintained to be not less than 1.0% or to be 1.0%-1.5%.

15. The fermentation method according to claim 5, wherein the seed solution is fermented in the fermentation medium, and the fermentation is performed at a temperature of not lower than 10° C. or not lower than 20° C., or a temperature of 20-60° C., or 20-50° C., or 20-40° C., or 30-50° C., or 30-40° C., or 35-40° C., or 37° C.

* * * * *

SEQUENCE LISTING

```
Sequence total quantity: 1
SEQ ID NO: 1            moltype = DNA  length = 1398
FEATURE                 Location/Qualifiers
source                  1..1398
                        mol_type = other DNA
                        organism = Bacillus natto
SEQUENCE: 1
tgcaagtcga gcggacagat gggagcttgc tccctgatgt tagcggcgga cgggtgagta  60
acacgtgggt aacctgcctg taagactggg ataactccgg gaaaccgggg ctaataccgg  120
atggttgttt gaaccgcatg gttcaaacat aaaaggtggc ttcggctacc acttacagat  180
ggacccgcgg cgcattagct agttggtgag gtaacggctc accaaggcaa cgatgcgtag  240
ccgacctgag agggtgatcg gccacactgg gactgagaca cggcccagac tcctacggga  300
ggcagcagta gggaatcttc cgcaatggac gaaagtctga cggagcaacg ccgcgtgagt  360
gatgaaggtt ttcggatcgt aaagctctgt tgttagggaa gaacaagtac cgttcgaata  420
gggcggtacc ttgacggtac ctaaccagaa agccacggct aactacgtgc cagcagccgc  480
ggtaatacgt aggtggcaag cgttgtccgg aattattggg cgtaaagggc tcgcaggcgg  540
tttcttaagt ctgatgtgaa agcccccggc tcaaccgggg agggtcattg gaaactgggg  600
aacttgagtg cagaagagga gagtggaatt ccacgtgtag cggtgaaatg cgtagagatg  660
tggaggaaca ccagtggcga aggcgactct ctggtctgta actgacgctg aggagcgaaa  720
gcgtggggag cgaacaggat tagataccct ggtagtccac gccgtaaacg atgagtgcta  780
agtgttaggg ggtttccgcc cctttagtgc tgcagctaac gcattaagca ctccgcctgg  840
ggagtacggt cgcaagactg aaactcaaag gaattgacgg gggcccgcac aagcggtgga  900
gcatgtggtt taattcgaag caacgcgaag aaccttacca ggtcttgaca tcctctgaca  960
atcctagaga taggacgtcc ccttcggggg cagagtgaca ggtggtgcat ggttgtcgtc  1020
agctcgtgtc gtgagatgtt gggttaagtc ccgcaacgag cgcaaccctt gatcttagtt  1080
gccagcattc agttgggcac tctaaggtga ctgccggtga caaaccggag gaaggtgggg  1140
atgacgtcaa atcatcatgc cccttatgac ctgggctaca cacgtgctac aatggacaga  1200
acaaagggca gcgaaaccgc gaggttaagc caatcccaca aatctgttct cagttcggat  1260
cgcagtctgc aactcgactg cgtgaagctg gaatcgctag taatcgcgga tcagcatgcc  1320
gcggtgaata cgttcccggg ccttgtacac accgcccgtc acaccacgag agtttgtaac  1380
acccgaagtc ggtgaggt                                                1398
```